United States Patent
Kopach et al.

(10) Patent No.: US 10,287,287 B2
(45) Date of Patent: May 14, 2019

(54) PROCESS DEVELOPMENT OF A PYRIDINE-CONTAINING NK-1 RECEPTOR ANTAGONIST

(71) Applicant: ELI LILLY AND COMPANY, Indianapolis, IN (US)

(72) Inventors: Michael E. Kopach, Greenwood, IN (US); Thomas Michael Wilson, Speedway, IN (US); Michael Edward Kobierski, Greenwood, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 0 days.

(21) Appl. No.: 15/745,461

(22) PCT Filed: Aug. 17, 2016

(86) PCT No.: PCT/US2016/047362
§ 371 (c)(1),
(2) Date: Jan. 17, 2018

(87) PCT Pub. No.: WO2017/031215
PCT Pub. Date: Feb. 23, 2017

(65) Prior Publication Data
US 2018/0237433 A1  Aug. 23, 2018

Related U.S. Application Data

(60) Provisional application No. 62/206,239, filed on Aug. 17, 2015.

(51) Int. Cl.
| | | |
|---|---|---|
| C07D 471/04 | (2006.01) | |
| C07D 401/14 | (2006.01) | |
| C07D 401/04 | (2006.01) | |
| C07D 401/06 | (2006.01) | |
| C07D 213/61 | (2006.01) | |

(52) U.S. Cl.
CPC ......... *C07D 471/04* (2013.01); *C07D 213/61* (2013.01); *C07D 401/04* (2013.01); *C07D 401/06* (2013.01); *C07D 401/14* (2013.01)

(58) Field of Classification Search
CPC .................................................. C07D 471/04
See application file for complete search history.

(56) References Cited

FOREIGN PATENT DOCUMENTS

| WO | 03091226 A1 | 11/2003 |
| WO | 2005042515 A1 | 5/2005 |
| WO | 2006083711 A1 | 8/2006 |
| WO | 2008079600 A1 | 7/2008 |

OTHER PUBLICATIONS

International Search Report and Written Opinion for PCT Application No. PCT/US2016/047362 dated Nov. 22, 2016, 15 pages.

*Primary Examiner* — Shawquia Jackson
(74) *Attorney, Agent, or Firm* — Hoffman Warnick LLC

(57) ABSTRACT

The disclosure provides process developments and novel routes for the preparation of the NK-1 receptor antagonist, Compound (I) and intermediates in those routes.

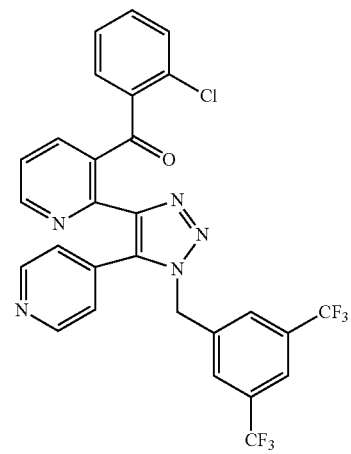

(I)

20 Claims, No Drawings

PROCESS DEVELOPMENT OF A PYRIDINE-CONTAINING NK-1 RECEPTOR ANTAGONIST

CROSS REFERENCE TO RELATED APPLICATIONS

This application claims the benefit of U.S. Provisional Application No. 62/206,239, filed Aug. 17, 2015, the entirety of which is incorporated herein as though fully set forth.

BACKGROUND OF THE INVENTION

The invention relates generally to process developments for pyridine-containing drug candidates. More particularly, the invention relates to process developments for the NK-1 receptor antagonist Compound (I).

Tachykinins are a family of peptides that are widely distributed in both the central and peripheral nervous systems. These peptides exert a number of biological effects through actions at tachykinin receptors. The role of the NK-1 receptor subtype in numerous disorders of the central nervous system and the periphery has been thoroughly demonstrated in the art. For instance, NK-1 receptors are believed to play a role in depression, anxiety, and central regulation of various autonomic, as well as cardiovascular and respiratory functions. NK-1 receptors in the spinal cord are believed to play a role in pain transmission, especially the pain associated with migraine and arthritis. In the periphery, NK-1 receptor activation has been implicated in numerous disorders, including various inflammatory disorders, asthma, and disorders of the gastrointestinal and genitourinary tract.

There is an increasingly wide recognition that selective NK-1 receptor antagonists would prove useful in the treatment of many diseases of the central nervous system and the periphery. While many of these disorders are being treated by new medicines, there are still many shortcomings associated with existing treatments. For example, the newest class of anti-depressants, selective serotonin reuptake inhibitors (SSRIs), are increasingly prescribed for the treatment of depression; however, SSRIs have numerous side effects, including nausea, insomnia, anxiety, and sexual dysfunction. This could significantly affect patient compliance rate. As another example, current treatments for chemotherapy-induced nausea and emesis, such as the 5-HT3 receptor antagonists, are ineffective in managing delayed emesis. The development of NK-1 receptor antagonists will therefore greatly enhance the ability to treat such disorders more effectively. One such NK-1 receptor antagonist is the compound depicted below as the compound of Formula (I)

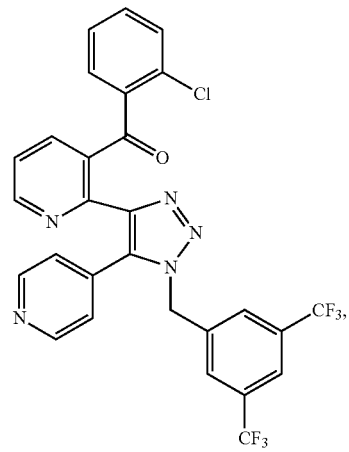

disclosed in U.S. Pat. No. 7,320,994 and known as {2-[1-(3,5-bistrifluoromethylbenzyl)-5-pyridin-4-yl-1H-[1,2,3]triazol-4-yl]-pyridin-3-yl}-(2-chlorophenyl)-methanone, and alternatively as Methanone, [2-[1-[[3,5-bis(trifluoromethyl)phenyl]methyl]-5-(4-pyridinyl)-1H-1,2,3-triazol-4-yl]-3-pyridinyl](2-chlorophenyl)-.

In International Patent Application Publication No. WO2005/042515, crystalline Forms IV and V of the compound of Formula (I) are identified. A process is also provided for preparation of the compound of Formula (I), comprising reacting (2-chlorophenyl)-[2-(2-hydroxy-2-pyridin-4-yl-vinyl)pyridin-3-yl]methanone or a phosphate salt thereof with 1-azidomethyl-3,5-bistrifluoromethylbenzene in the presence of a suitable base and a solvent. However, use of this process results in shortcomings for synthesis on a commercial scale.

BRIEF DESCRIPTION OF THE INVENTION

A first aspect of the disclosure provides a method of preparing Compound (I), the method comprising treating a mixture of zinc dust and dimethylformamide with 1,2-dibromoethane and heating the mixture; cooling the mixture to ambient temperature and treating the mixture with trimethylsilyl chloride; adding zinc chloride in diethyl ether to the mixture; adding the Compound (IIa) to the mixture; heating the mixture and treating the mixture with 1,2-dibromoethane and trimethylsilyl chloride; adding tetrakis(triphenylphosphine)palladium(0) and Compound (IIIa) to the mixture; and heating to form Compound (I).

A second aspect of the disclosure provides a method of preparing Compound (IIa), the method including: adding a solution of iodine monochloride in 1,2-dichloroethane to a solution of Compound (IV) in 1,2-dichloroethane to form a slurry, and heating the slurry to a temperature of about 75° C., then cooling the slurry to ambient temperature, collecting a resulting solid, and treating the solid with sodium thiosulfate to yield the Compound (IIa). In some embodiments, the process further comprises purifying the Compound (IIa) by silica gel chromatography.

A third aspect of the disclosure provides a method of preparing Compound (IV), the method comprising: heating a mixture of Compound (V) and Compound (VI), in some embodiments to a temperature of about 95-105° C.; adding heptane to the mixture; and crystallizing Compound (IV) from the heptane.

A fourth aspect of the disclosure provides a method of preparing the starting material Compound (VI) according to a process comprising: adding zinc bromide to tetrahydrofuran cooled to between about 0 to 10° C. to form a solution; adding 4-bromopyridine hydrochloride, triphenylphosphine, and palladium (II) chloride to the cooled solution; further adding triethylamine and trimethylsilylacetylene; combining the reaction mixture with hexanes, and treating the reaction mixture with NH₄OH; washing an organic phase of the reaction mixture first with NH₄OH and then with water; neutralizing the organic phase with hydrochloric acid; drying the organic phase with sodium sulfate and concentrating to a slurry; combining the slurry with hexanes to give a precipitate; filtering the precipitate out of the slurry and concentrating a filtrate; and distilling the filtrate to produce Compound (VI).

A fifth aspect of the disclosure provides a method for preparing the Compound (IIIa) according to a process comprising adding 2-bromopyridine to LDA in THF at about −70° C.; adding Compound (VII) in THF; and crystallizing Compound (IIIa) from isopropyl alcohol and heptane. In some embodiments, the Compound (VII) is prepared according to a process comprising adding morpholine to toluene and Compound (IX) to form a slurry; and adding pyridine to the slurry.

A sixth aspect of the disclosure provides a method for preparing Compound (I)

(I)

that according to a process that comprises contacting Compound (XII)

(XII)

with Compound (III)

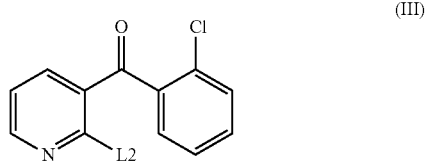

(III)

in the presence of a transition metal catalyst in an aprotic and substantially anhydrous solvent. L2 is a leaving group, and L1 is either a leaving group or

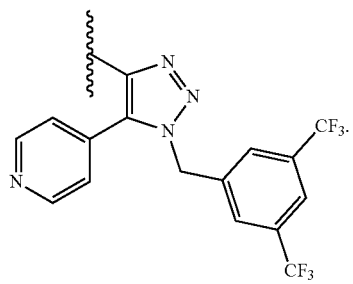 [SMILES: *c1nnn(Cc2cc(C(F)(F)F)cc(C(F)(F)F)c2)c1-c1ccncc1]

In some embodiments, the transition metal catalyst is a palladium, nickel, cobalt, iron or copper catalyst. In some embodiments, the solvent is N,N-dimethylformamide, N,N-dimethylacetamide, tetrahydrofuran, diisopropyl ether, toluene, anisole, t-butylmethyl ether, diethyl ether, 1,4-dioxane, 1,2-dimethoxyethane, N-methylpyrrolidone or dimethylsulfoxide. In some embodiments, a phosphine is included in the reaction mixture. In some embodiments, a zinc halide such as $ZnCl_2$ is included in the reaction mixture. In some embodiments, lithium chloride is included in the reaction mixture. In some embodiments, L1 is selected from the group consisting of I, Br, Cl, $C_1$-$C_2$ alkanesulfonate, $C_1$-$C_2$ perfluoromethanesulfonate, $FSO_3$, and

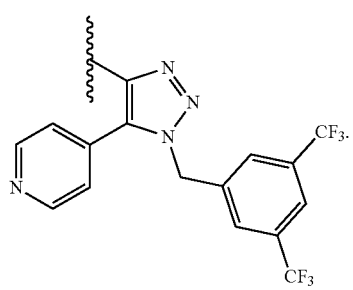 [SMILES: *c1nnn(Cc2cc(C(F)(F)F)cc(C(F)(F)F)c2)c1-c1ccncc1]

In some embodiments, L2 is selected from the group consisting of I, Br, Cl, $C_1$-$C_2$ alkanesulfonate, $C_1$-$C_2$ perfluoromethanesulfonate, and acetate.

These and other aspects, advantages and salient features of the invention will become apparent from the following detailed description, which, when taken in conjunction with the annexed drawings, where like parts are designated by like reference characters throughout the drawings, disclose embodiments of the invention.

DETAILED DESCRIPTION OF THE INVENTION

The terms and abbreviations use in the preparations and examples that follow have their normal meanings unless designated otherwise. Abbreviations and terms used herein may include but are not limited to the following: MTBE refers to tert-butyl methyl ether, MeOH refers to methanol, TMSCl refers to trimethylsilyl chloride, IPA refers to isopropyl alcohol, LDA refers to lithium diisopropylamide, THF refers to tetrahydrofuran, NH₄OH refers to ammonium hydroxide, DMF refers to N,N-dimethylformamide, EtOAc refers to ethyl acetate, H₂O refers to water, CH₃CN refers to acetonitrile, CDCl₃ refers to deuterated chloroform, NaOH refers to sodium hydroxide, HCl refers to hydrochloric acid, NaHCO₃ refers to sodium bicarbonate, DMSO refers to dimethylsulfoxide, RT refers to room temperature, LRMS refers to low resolution mass spectrometry, and NMR refers to nuclear magnetic resonance spectroscopy. As used herein, "heptanes" refers to a mixture of n-heptane and its branched isomers.

The following examples provide new routes for the synthesis of the compound of formula (I)

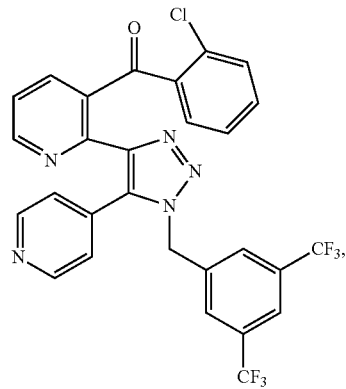
(I)

including a process comprising contacting Compound (XII)

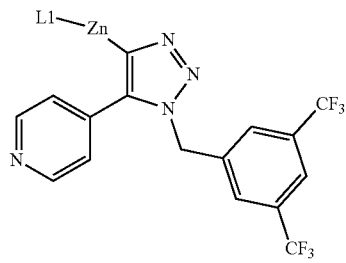
(XII)

with Compound (III)

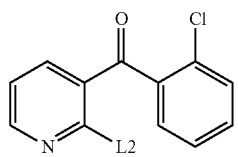
(III)

in the presence of a transition metal catalyst in an aprotic and substantially anhydrous solvent. L2 is a leaving group, and L1 is either a leaving group or

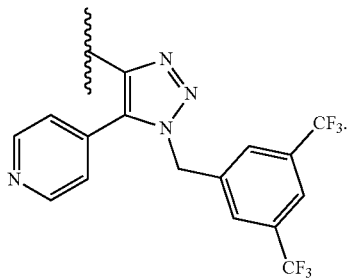 [SMILES: *c1nnn(Cc2cc(C(F)(F)F)cc(C(F)(F)F)c2)c1-c1ccncc1]

In some embodiments, the transition metal catalyst may be a palladium, nickel, cobalt, iron or copper catalyst, and the solvent may be N,N-dimethylformamide, N,N-dimethylacetamide, tetrahydrofuran, diisopropyl ether, toluene, anisole, t-butylmethyl ether, diethyl ether, 1,4-dioxane, 1,2-dimethoxyethane, N-methylpyrrolidone or dimethylsulfoxide. Particularly, the solvent may be N,N-dimethylformamide. In some embodiments, a phosphine is included in the reaction mixture. In some embodiments, a zinc halide such as ZnCl₂ is included in the reaction mixture. In some embodiments, lithium chloride is included in the reaction mixture. In some embodiments, L1 is selected from the group consisting of I, Br, Cl, C₁-C₂ alkanesulfonate, C₁-C₂ perfluoromethanesulfonate, FSO₃, and

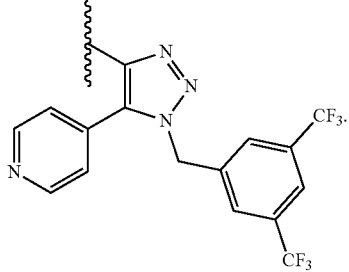 [SMILES: *c1nnn(Cc2cc(C(F)(F)F)cc(C(F)(F)F)c2)c1-c1ccncc1]

Particularly, L1 may be I. In some embodiments, L2 is selected from the group consisting of I, Br, Cl, C₁-C₂ alkanesulfonate, C₁-C₂ perfluoromethanesulfonate, and acetate. Particularly, L2 may be Br. Particularly, the transition metal catalyst may be a palladium or nickel catalyst. More particularly, the transition metal catalyst may be a palladium catalyst. Particularly, a phosphine may be included in the reaction mixture. Even more particularly, the catalyst may be Pd(PPh₃)₄.

In the process, all reaction steps are carried out under ambient conditions except as otherwise noted.

In one embodiment, the process may include treating a mixture of zinc dust and dimethylformamide with 1,2-dibromoethane and heating the mixture to about 50° C. to about 100° C., e.g., about 60° C. to about 70° C., e.g., about 65° C., e.g., for about 1 to 10 minutes, e.g., about 2-5 minutes, e.g., 3 minutes, under ambient pressure conditions. Following heating, the mixture may then be cooled to ambient temperature and treated with trimethylsilyl chloride, which may be added to the mixture for about 1 to 10 minutes, e.g., about 2-8 minutes, e.g., 5 minutes. Zinc chloride and a compound of formula (IIa)

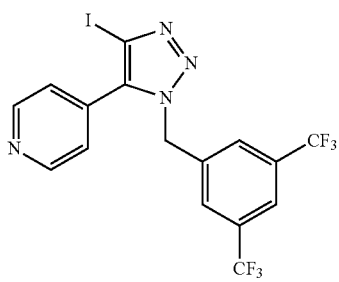

may then be added to the mixture and heated to about 50° C. to about 100° C., e.g., about 60° C. to about 70° C., e.g., about 65° C. 1,2-dibromoethane and trimethylsilyl chloride may then be added to the mixture and stirred, and the mixture allowed to react for about 8 hours to about 24 hours, e.g., about 12 hours to about 18 hours, e.g., about 16 hours. Following the reaction, tetrakis(triphenylphosphine)palladium(0) and a compound of formula (IIIa)

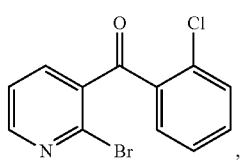

may be added and heated to about 50° C. to about 100° C., e.g., about 60° C. to about 70° C., e.g., about 65° C. to form the compound of formula (I).

Other methods that can be used to prepare activated zinc dust for the purpose of preparing Compound (XII), such as the Rieke method, are described in Haas, D., Hammann, J. M., Greiner, R., and Knochel, P., Recent Developments in Negishi Cross-Coupling Reactions, *ACS Catal.* 2016, 6, 1540-1552 (Haas, D. et al. 1), which is incorporated herein in its entirety by reference. Other methods for preparing organozinc compounds, such as by transmetallation of a Grignard or lithium species, are described in Haas, D. et al. 1. Alternative reaction conditions for the Negishi cross-coupling reaction are also described in Haas, D. et al. 1, and in Haas, D., Hammann, J. M., Lutter, F. H. and Knochel, P., *Angew. Chem. Intl. Ed. Engl.* 2016, 55, 3809-3812 (Haas, D. et al. 2), which is incorporated herein in its entirety by reference.

A particular illustrative example, in which L1 is I, L2 is Br; and the transition metal catalyst is a triphenylphosphine Pd catalyst, is provided in the examples below.

EXAMPLES

Example 1: Preparation of Compound (I) Via Negishi Coupling Route

Example 1 provides a scheme including preparations 1A-1D, described below, for the synthesis of the compound of Formula (I) and intermediates used in the route. An overview of the scheme is as follows:

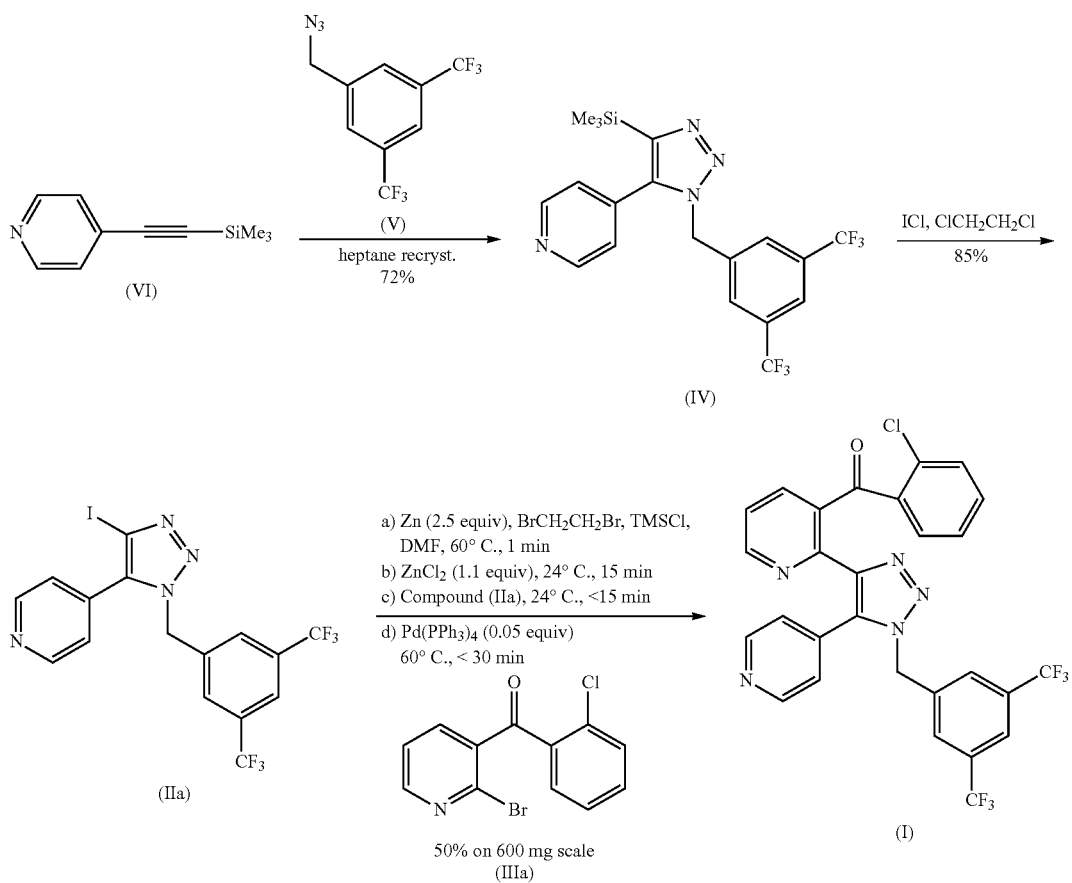

Example 1A: Preparation of Compound (I)

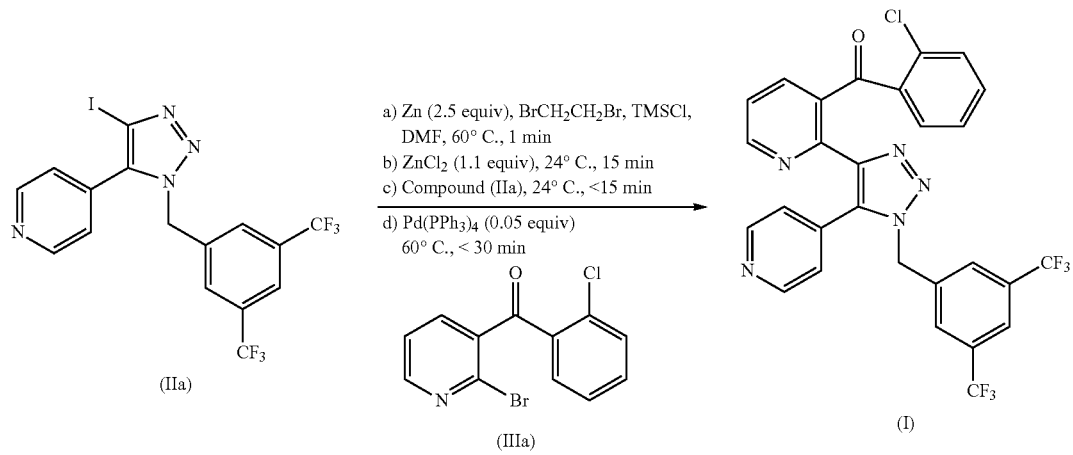 [SMILES: FC(F)(F)c1cc(Cn2nnc(I)c2-c2ccncc2)cc(C(F)(F)F)c1 ; "(IIa)" ; O=C(c1ccccc1Cl)c1cccnc1Br ; O=C(c1ccccc1Cl)c1cccnc1-c1nnn(Cc2cc(C(F)(F)F)cc(C(F)(F)F)c2)c1-c1ccncc1 ; "(I)"]

Zinc dust (200 mg, 3.06 mmol) combined with 2.0 mL of dimethylformamide was treated with 0.010 mL of 1,2-dibromoethane and heated to 65° C. for 3 minutes. The mixture was cooled to ambient temperature and treated with 0.010 mL of trimethylsilyl chloride. After 5 minutes, 1.26 mL of 1M zinc chloride in diethyl ether was added to the mixture followed by Compound (IIa) (600 mg, 1.20 mmol). The mixture was heated to 65° C. and further treated with 0.020 mL each of 1,2-dibromoethane and trimethylsilyl chloride. After 2.5 hours, via HPLC chromatogram, the reaction showed some formation of the zincate and was allowed to stir at ambient temperature for 16 hours. At this time tetrakis(triphenylphosphine)palladium(0) (70 mg, 0.06 mmol), Compound (IIIa) (357 mg, 1.20 mmol) were added to the reaction and the mixture heated to 65° C. HPLC analysis showed the formation of Compound (I) in the reaction.

Example 1B: Preparation of Compound (IIa)

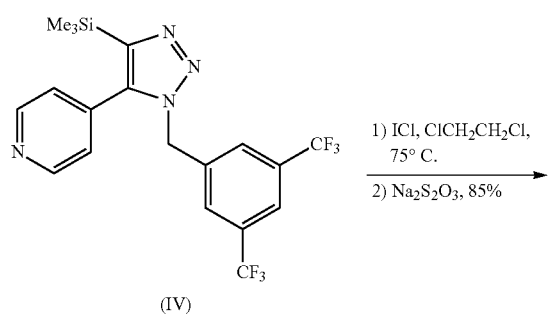

To a solution of Compound (IV) (8.00 g, 18 mmol) in 40 mL of 1,2-dichloroethane was added a solution of iodine monochloride (10.7 g, 65.9 mmol) in 40 mL of 1,2-dichloroethane resulting in a slurry. The slurry was heated to 75° C. for 4 hours then cooled to ambient temperature. The solids were collected by filtration, washed with heptane, then combined with 90 mL of ethyl acetate and 80 mL of saturated sodium thiosulfate solution. The organic phase was washed with saturated sodium chloride solution and dried with sodium sulfate. The mixture was concentrated to yield 7.80 g (87%) of Compound (IIa) as a yellow solid. The product could be further purified by silica gel chromatography. Thus 2.0 g of yellow solid was dissolved in dichloromethane and charged onto a silica gel column. The product was eluted using tert-butyl methyl ether to provide 1.87 g (93% recovery) of Compound (IIa) as a white powder. Analytical data: Iodine monochloride complex: $^1$H NMR (500 MHz, DMSO-$d_6$) δ 8.80 (2H), 8.05 (1H), 7.77 (2H), 7.59 (2H), 5.86 (2H). Uncomplexed: $^1$H NMR (500 MHz, DMSO-$d_6$) δ 8.71 (2H), 8.03 (1H), 7.74 (2H), 7.44 (2H), 5.86 (2H).

It was observed that the iodination proceeded smoothly as a suspension in 1,2-dichloroethane with ICl (4.0 equiv) at 75° C. An ICl-Compound (IIa) complex was initially isolated by filtration. Compound (IIa) was then obtained in approximately 85% yield by treatment of the ICl-Compound (IIa) complex with sodium thiosulfate. This protocol provided a viable means of isolation of Compound (IIa) without the use of DMF.

Example 1C: Preparation of Silyl Substituted Triazole (Compound IV)

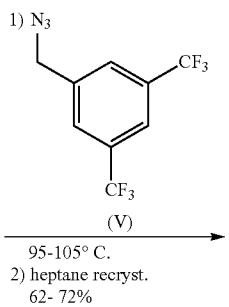

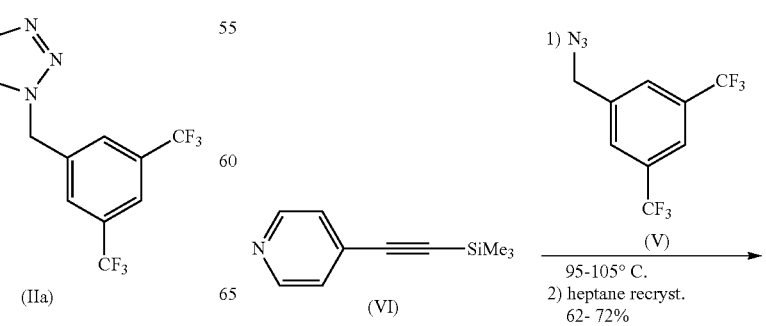

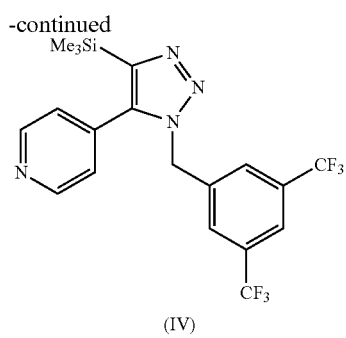

(IV)

A mixture of Compound (V) (8.07 g, 30.0 mmol) and Compound (VI) (5.12 g, 29.2 mmol) was heated to 100° C. for 18 hours. To the mixture was added 40 mL of heptane and the reaction was allowed to cool with rapid stirring. After 1 hour the solids were collected by filtration and washed with heptane then dried to 9.30 g (72%) of Compound (IV) as a tan solid. Analytical data: $^1$H NMR (500 MHz, DMSO-$d_6$) δ 8.66 (2H), 8.04 (1H), 7.67 (2H), 7.32 (2H), 5.72 (2H), 0.08 (9H).

It was further found that combining Compound (V) and Compound (VI) (neat) and heating at 95-105° C. afforded a 92:8 mixture of regioisomers as shown below:

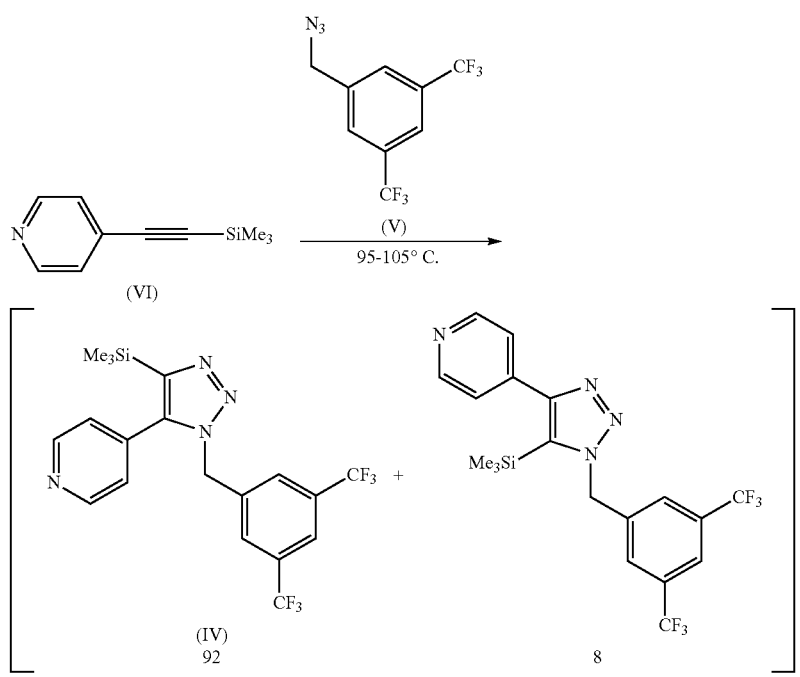

Crystallization of the mixture from heptane afforded Compound (IV) in 62-72% yield, thus obviating the need for chromatography to isolate Compound (IV).

Example 1D: Preparation of Starting Material Compound (VI)

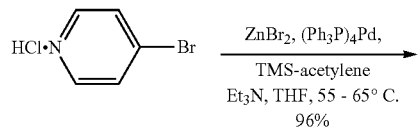

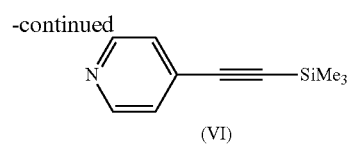

(VI)

Zinc bromide (502 g, 2.23 mole) was added in approximately 100 g portions to 2.0 L of tetrahydrofuran cooled to between 0 and 10° C. To this cooled solution was added 4-bromopyridine hydrochloride (200 g, 1.02 mol), triphenylphosphine (54 g, 0.206 mol), and palladium (II) chloride (9.00 g, 0.0508 mol). Triethylamine (813 g, 8.03 mol) was then added at a rate to maintain the reaction temperature at less than 10° C., and finally trimethylsilylacetylene (202 g, 2.05 mol) was added. The mixture was heated to 60° C. for 4.5 hours. The reaction was cooled to −5° C. and combined with 2.0 L of hexanes and treated with 2 L of 7.4 M NH$_4$OH. Some solids were formed and were removed as much as possible with the aqueous phase. The organic phase was again washed with 2.0 L of 7.4 M NH$_4$OH, followed by 2 washes with 500 mL of water, neutralized with 1.7 L of 3 M hydrochloric acid, dried with sodium sulfate, and concentrate to a thick slurry. The slurry was combined with 1.0 L of hexanes to give a precipitate. The precipitate was removed by filtration and the filtrate was concentrated to 209 g of dark oil. The product was purified by distillation (0.2 torr, 68° C.) to give 172 g (96%) of Compound (VI) as colorless oil. Analytical data: $^1$H NMR (500 MHz, DMDO-$d_6$) δ 8.57 (2H), 7.40 (2H), 0.23 (9H).

Example 2—Preparation of Compound (IIIa)

Example 2 provides a morpholine amide route for the synthesis of Compound (IIIa). In this approach, morpholine amide (Compound VII) was prepared from 2-chlorobenzoyl chloride (Preparation 2A). Metallation of 2-bromopyridine with LDA (1.09 equiv.) in THF at −70° C. followed by addition of (Compound VII) afforded Compound (IIIa) in 37% yield after crystallization from IPA/heptane (Preparation 2B). This sequence provides a direct route to Compound (IIIa), and a means to isolate Compound (IIIa) without the use of chromatography. Compound (IIIa) may then be used to form Compound (I) as shown in Example 1A above (Preparation 2C).

Preparation 2A: Preparation of Compound (VII)

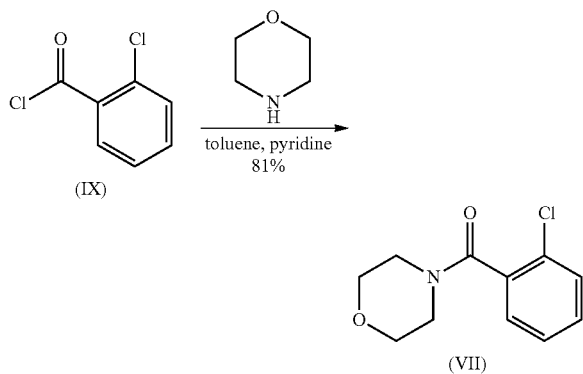

Toluene (1.5 L) was added to Compound (IX) (150 g, 0.86 mol) and cooled to 10° C. Morpholine (82 mL, 0.94 mol) was added to the clear solution over 10 minutes. The resulting white slurry was stirred for 20 minutes then pyridine (92 mL, 1.2 mol) was added dropwise over 20 minutes. The cloudy white mixture was stirred in a cold bath for 1 hour. Water (600 mL) was added in a single portion and the cold bath removed. The mixture was stirred for 20 minutes and the layers are separated. The organic layer was washed with a mixture of 1 N HCl and water (2:1, 500 mL:250 mL). The pH of the aqueous layer was ~2. The organic layer was washed with a mixture of saturated NaHCO$_3$ and water (1:1, 100 mL:100 mL). The pH of the aqueous layer was ~9. The layers were separated. The organic layer was concentrated in vacuo to an oil. The oil was dissolved in IPA (70 mL) and heated at 60° C. for 30 min. The clear solution was allowed to cool to 30° C., then heptane (700 mL, 4.7 v) was added dropwise. The resulting slurry was stirred at RT for 2 hours then cooled to 0° C. for 1 hour. The slurry was filtered at RT, washed with heptane then dried under vacuum at 30° C. overnight. Compound (VII) (156.2 g, 81%) was obtained as a white solid. Analytical data: $^1$H NMR (500 MHz, CDCl$_3$) δ 7.42-7.40 (m, 1H), 7.35-7.29 (m, 3H), 3.91-3.87 (m, 1H), 3.80-3.76 (m, 3H), 3.71 (ddd, J=11.5, 6.8, 3.3 Hz, 1H), 3.60 (ddd, J=11.2, 6.4, 3.4 Hz, 1H), 3.28 (ddd, J=13.4, 6.3, 3.2 Hz, 1H), 3.22 (ddd, J=13.7, 6.8, 3.3 Hz, 1H); LRMS (ES+) calcd for C$_{11}$H$_{13}$F$_6$ClNO$_2$ (M+H)$^+$ 226.1, found 225.9 m/z.

Preparation 2B: Preparation of Compound (IIIa)

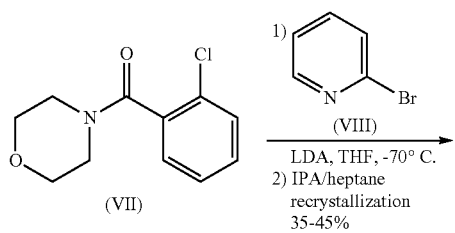

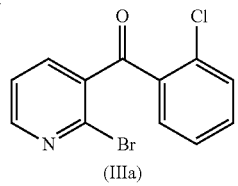

THF (75 mL) was added to diisopropylamine (4.9 mL, 34.8 mmol) and cooled to a temperature of –70° C. under N$_2$ atmosphere. 2.5 M n-BuLi in hexanes (13.9 mL, 34.8 mmol) was added in a single portion (a 30-40° C. exotherm) to the clear solution and cooled back to –70° C. Compound (VIII) (5.0 g, 31.6 mmol) was added neat to the LDA solution (a 2 to 5° C. exotherm) followed by a THF (10 mL) rinse, keeping T<–65° C. This clear yellow solution was stirred at –70° C. for 15 min. Compound (VII) (7.1 g, 31.6 mmol) in THF (30 mL) was added keeping T<–65° C. The resulting clear orange solution was stirred at –70° C. for 3 hours. MeOH (3 mL) was added to quench reaction mixture and the cold bath was removed. 5 N HCl (25 mL) was added to the reaction solution. MTBE (25 mL) was added, and the layers were separated. The organic layer was washed with water (25 mL×2). The organic layer was dried over MgSO$_4$ and filtered. The organic layer was concentrated in vacuo to an orange oil. The oil was dissolved in IPA (15 mL, 3 vol) at ambient temperature. Heptane (25 mL) was added dropwise and the resulting slurry was stirred at RT for 1 hour. The slurry was cooled to 0° C. for 1 hour and filtered. The filter cake was rinsed with chilled heptane (20 mL) and dried under vacuum at 30° C. overnight. Compound (IIIa) (4.25 g, 45%) was obtained as a yellow solid.

Several reactions were run at different temperatures and with different addition rates of Compound (VII). If the reaction temperature was maintained below –65° C. and Compound (VII) was added in <5 min, it was found that the reaction worked well. If the temperature was increased and/or the addition time of Compound (VII) was increased, then yields suffered, and the work-up was complicated by emulsions.

Preparation 2C: Preparation of Compound (I)

Compound (IIIa) may then reacted with Compound (IIa) to produce Compound (I) as shown in Preparation 1A.

Example 3

Example 3 describes a new route for the synthesis of an intermediate free base, which may be used to form Compound (I) as described further below.

Example 3A: Preparation of Starting Material (Compound X) from 2-Chloronicotinonitrile

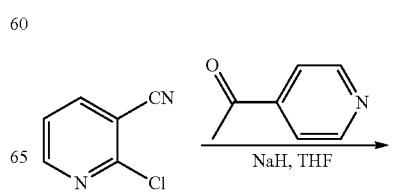

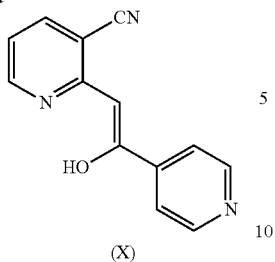

(X)

A mixture of NaH (40.0 g, 1 mol, 60% dispersion in mineral oil) and 2-chloronicotinonitrile (69.3 g, 500 mmol) in THF (1 L) was heated to reflux. A solution of 4-acetylpyridine (60.6 g, 500 mmol) in THF (400 mL) was added over a period of 40 min. The resulting dark brown mixture was stirred at reflux for ~2 h. The heating mantle was then removed, and AcOH (58 mL, 1 mol) was added. EtOAc (1 L) and H$_2$O (1 L) were then added, and the layers were separated. The organic layer was concentrated to afford an oily solid. CH$_3$CN (500 mL) was added, and the mixture was stirred for 30 min. H$_2$O (1 L) was then added. The mixture was stirred for 1 h then filtered. The solid was rinsed with 2:1 CH$_3$CN—H$_2$O (900 mL) and hexanes (400 mL) then dried under vacuum at 45° C. overnight to afford 61.4 g (55% yield) of Compound (X) as yellow solid. Compound (X) exists as an approximate 95:5 enol-ketone mixture in CDCl$_3$. Analytical data for enol: IR (CHCl$_3$): 3024, 2973, 2229, 1631, 1597, 1579, 1550, 1497; $^1$H NMR (500 MHz, CDCl$_3$) δ 8.69 (dd, J=4.4, 1.7 Hz, 2H), 8.55 (dd, J=5.2, 1.8 Hz, 1H), 7.97 (dd, J=7.9, 1.8 Hz, 1H), 7.70 (dd, J=4.6, 1.5 Hz, 2H, 7.17 (dd, J=7.8, 5.0 Hz, 1H), 6.59 (s, 1H); LRMS (ES+) calcd for C$_{13}$H$_{10}$N$_3$O (M+H)$^+$ 224.1, found 224.0 m/z.

Preparation 3B: Preparation of Compound (XI)

Preparation 3B(1)

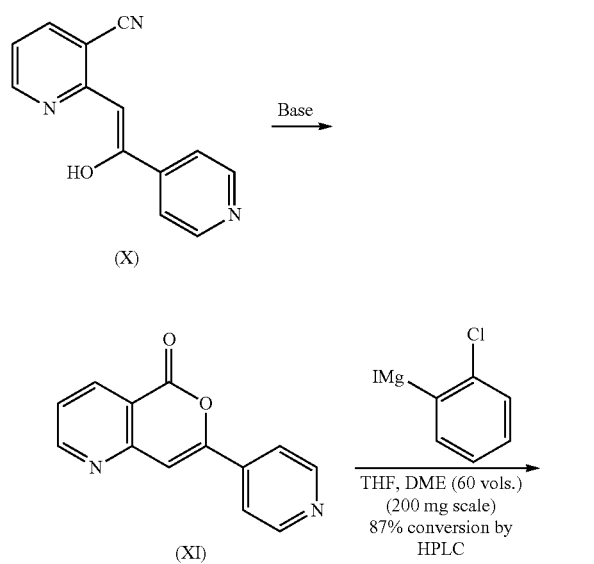

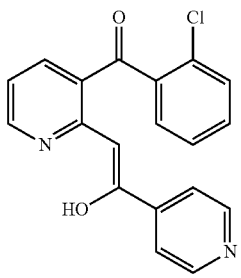

Compound (XI) may be prepared using Compound (X).

Preparation 3B(2)

Alternatively, the following procedure for the conversion of nitrile into an acid which may also yield compound (XI). A mixture of Compound (X) (1 eq) and NaOH (1.5 eq) in 1:1 H$_2$O-EtOH (3.5 mL/g of Compound (X)) was heated at 65° C. overnight. The reaction mixture was cooled to RT then added to CH$_2$Cl$_2$ (12.5 mL/g of Compound (X)) and H$_2$O (12.5 mL/g of Compound (X)). Conc. HCl (2.5 mL/g of Compound (X)) was then added, and the layers were separated. The aqueous layer was extracted with CH$_2$Cl$_2$ (10 mL/g of Compound (X)). The combined organic extracts were washed with H$_2$O (12.5 ml/g of Compound (X)), dried (MgSO$_4$), filtered and concentrated to afford Compound (XI).

Preparation 3C

Compound Compound (XI) may then be converted into a Stage C intermediate free base, with observed 87% conversion in Grignard reaction as shown above. A complete synthesis route for Compound (I) starting from compound Compound (XI) is depicted below.

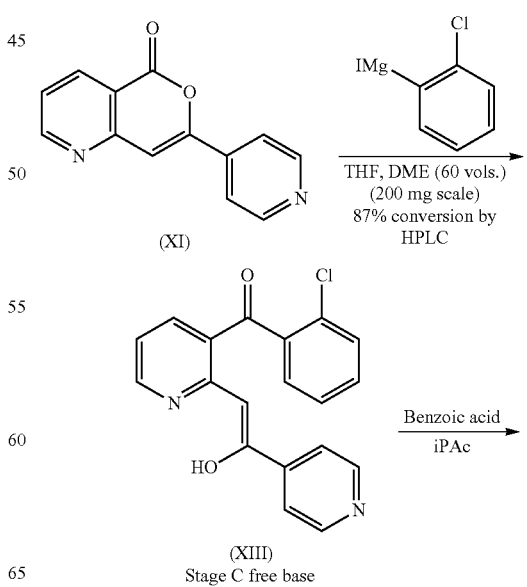

-continued

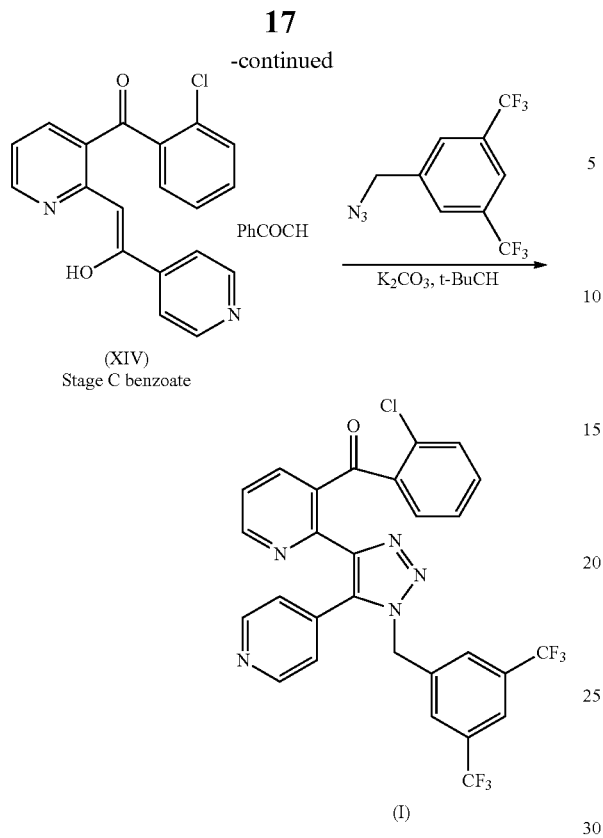

Detailed experimental procedures for the synthesis of benzoate salt and final step are given in International Patent Application Publication WO 2008/079600 A1.

As used herein, the terms "first," "second," and the like, do not denote any order, quantity, or importance, but rather are used to distinguish one element from another, and the terms "a" and "an" herein do not denote a limitation of quantity, but rather denote the presence of at least one of the referenced item. The modifier "about" used in connection with a quantity is inclusive of the stated value and has the meaning dictated by the context (e.g., includes the degree of error associated with measurement of the particular quantity). The suffix "(s)" as used herein is intended to include both the singular and the plural of the term that it modifies, thereby including one or more of that term (e.g., the metal(s) includes one or more metals). Ranges disclosed herein are inclusive and independently combinable (e.g., ranges of "up to about 25 ml, or, more specifically, about 5 ml to about 20 ml," is inclusive of the endpoints and all intermediate values of the ranges of "about 5 ml to about 25 ml," etc.).

While various embodiments are described herein, it will be appreciated from the specification that various combinations of elements, variations or improvements therein may be made by those skilled in the art, and are within the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method of preparing Compound (I):

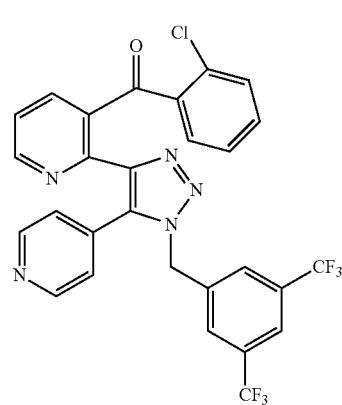

comprising:
contacting Compound (XII)

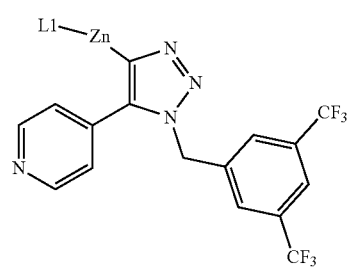

with Compound (III)

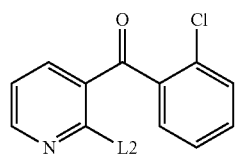

in the presence of a palladium, nickel, cobalt, iron or copper catalyst in an aprotic and substantially anhydrous solvent,
optionally in the presence of a phosphine,
optionally in the presence of $ZnCl_2$,
optionally in the presence of lithium chloride,
wherein L1 is selected from the group consisting of I, Br, Cl, $C_1$-$C_2$ alkanesulfonate, $C_1$-$C_2$ perfluoromethanesulfonate, $FSO_3$, and

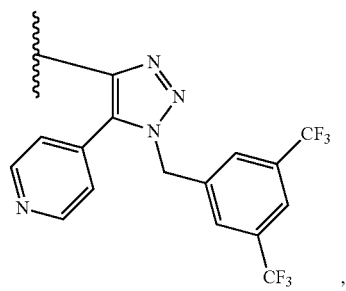 [SMILES: *c1nnn(Cc2cc(C(F)(F)F)cc(C(F)(F)F)c2)c1-c1ccncc1]

and

L2 is selected from the group consisting of I, Br, Cl, $C_1$-$C_2$ alkanesulfonate, $C_1$-$C_2$ perfluoromethanesulfonate, and acetate.

2. The method of claim 1, wherein the aprotic and substantially anhydrous solvent is selected from the group consisting of: N,N-dimethylformamide, N,N-dimethylacetamide, tetrahydrofuran, diisopropyl ether, toluene, anisole, t-butylmethyl ether, diethyl ether, 1,4-dioxane, 1,2-dimethoxyethane, N-methylpyrrolidone, and dimethylsulfoxide.

3. The method of claim 1, wherein the Compound (XII) is derived from a reaction of Compound (IIa)

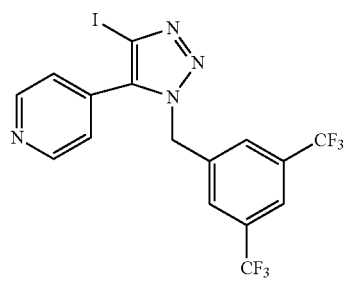

(IIa)

with activated zinc powder.

4. The method of claim 3, wherein the activated zinc powder is prepared according to a process comprising treating zinc dust in an aprotic and substantially anhydrous solvent with 1,2-dibromoethane or trimethylsilyl chloride.

5. The method of claim 3, wherein the activated zinc powder is contacted with $ZnCl_2$.

6. The method of claim 1, wherein the catalyst is a palladium catalyst containing a phosphine ligand, and the solvent is N,N-dimethylformamide.

7. The method of claim 1, comprising:
treating a mixture of zinc dust and dimethylformamide with 1,2-dibromoethane and heating the mixture;
cooling the mixture to ambient temperature and treating the mixture with trimethylsilyl chloride;
adding zinc chloride in diethyl ether to the mixture;
adding the Compound (IIa)

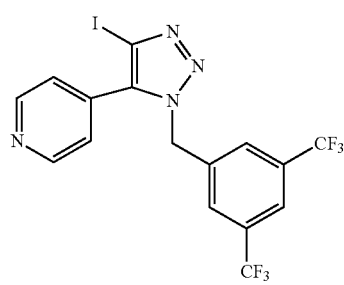

(IIa)

to the mixture;
heating the mixture and treating the mixture with 1,2-dibromoethane and trimethylsilyl chloride;
adding tetrakis(triphenylphosphine)palladium(0) and Compound (IIIa)

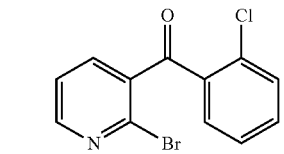

(IIIa)

to the mixture; and
heating to form Compound (I).

8. The method of claim 1, wherein the Compound (XII) is derived from Compound (IIa)

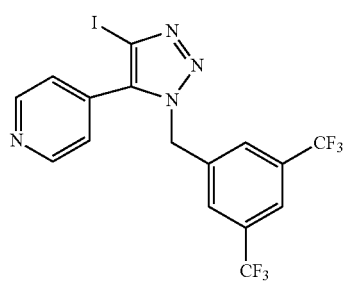

(IIa)

which is prepared according a process comprising:
contacting Compound (IV)

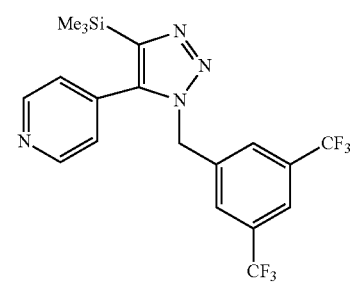

(IV)

with iodine monochloride.

9. The method of claim 8, wherein the process for preparing Compound (IIa) further comprises:
contacting Compound (IV) with iodine monochloride in 1,2-dichloroethane and heating the reaction mixture to a temperature of about 75° C. to form a slurry;
cooling the slurry to ambient temperature, collecting a resulting solid, and treating the solid with sodium thiosulfate to yield the Compound (IIa); and
purifying the Compound (IIa) by silica gel chromatography.

10. The method of claim 8, wherein the Compound (IV) is prepared according to a process comprising:

heating a mixture of Compound (V)

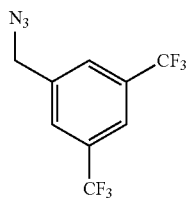

and Compound (VI)

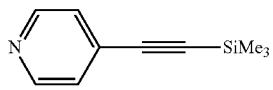

to a temperature of about 95-105° C.;
adding heptane to the mixture; and
crystallizing Compound (IV) from the heptane.

11. The method of claim 10, wherein the Compound (VI) is prepared according to a process comprising combining:
trimethylsilylacetylene;
4-bromopyridine or a salt thereof;
a zinc or copper catalyst;
a palladium catalyst;
a phosphine, if not already included in the palladium catalyst;
a base; and
a solvent.

12. The method of claim 11, wherein:
the 4-bromopyridine or the salt thereof is 4-bromopyridine hydrochloride;
the zinc or copper catalyst is $ZnBr_2$ or CuI;
the palladium catalyst is selected from the group consisting of:
$PdCl_2$,
$Pd(OAc)_2$,
$Pd(PPh_3)_4$,
$Pd(PPh_3)_2Cl_2$,
[1,2-bis(diphenylphosphino)ethane]-dichloropalladium(II),
(1,3-bis(diphenylphosphino)propane)palladium(II) chloride, and
[1,1'-bis(diphenylphosphino)ferrocene]dichloropalladium(II);
the base is selected from the group consisting of:
$CsCO_3$,
$K_2CO_3$,
$Na_2CO_3$, and
an amine; and
the solvent is selected from the group consisting of:
N,N-dimethylformamide,
N,N-dimethylacetamide,
tetrahydrofuran,
diisopropyl ether,
toluene,
anisole,
t-butylmethyl ether,
diethyl ether,
1,4-dioxane,
1,2-dimethoxyethane,
N-methylpyrrolidone, and
dimethylsulfoxide.

13. The method of claim 11, wherein the process for preparing Compound (VI) further comprises:
combining zinc bromide and the solvent, wherein the solvent is selected from the group consisting of: N,N-dimethylformamide, N,N-dimethylacetamide, tetrahydrofuran, diisopropyl ether, toluene, anisole, t-butylmethyl ether, diethyl ether, 1,4-dioxane, 1,2-dimethoxyethane, N-methylpyrrolidone, and dimethylsulfoxide;
adding 4-bromopyridine hydrochloride, triphenylphosphine, and palladium (II) chloride while maintaining the batch temperature between about 0° C. about 25° C.;
further adding triethylamine and trimethylsilylacetylene while maintaining the batch temperature between about 0° C. about 25° C.;
combining the reaction mixture with hexanes, and treating the reaction mixture with $NH_4OH$;
washing an organic phase of the reaction mixture first with $NH_4OH$ and then with water;
neutralizing the organic phase with an acid;
drying the organic phase, and concentrating to a slurry;
combining the slurry with hexanes to give a precipitate;
filtering the precipitate out of the slurry and concentrating a filtrate; and
distilling the filtrate to produce Compound (VI).

14. The method of claim 13, wherein the acid for neutralizing the organic phase is hydrochloric acid; and wherein the drying of the organic phase includes stirring with sodium sulfate or magnesium sulfate.

15. The method of claim 1, wherein the Compound (III) is Compound (IIIa)

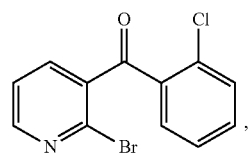

and

Compound (IIIa) is prepared according to a process comprising:
contacting 2-bromopyridine with lithium diisopropylamine (LDA) in tetrahydrofuran (THF) at about −70° C. to form lithiated 2-bromopyridine;
contacting the lithiated 2-bromopyridine with Compound (VII)

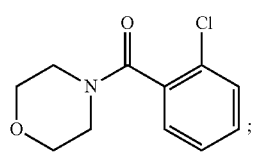

and crystallizing Compound (IIIa)

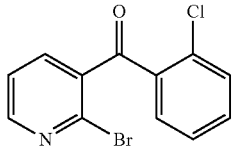
(IIIa)

from isopropyl alcohol and heptane, wherein the Compound (VII) is prepared according to a process comprising: combining morpholine, toluene, Compound (IX)

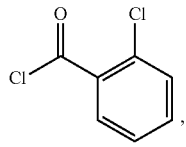
(IX)

and pyridine.

16. The method of claim 7, further comprising:

treating the mixture of zinc dust and dimethylformamide with 1,2-dibromoethane and heating the mixture to about 50° C. to about 100° C. for about 1 to 10 minutes at ambient pressure;

cooling the mixture to ambient temperature, adding trimethylsilyl chloride and agitating the mixture for about 1 to 10 minutes;

adding zinc chloride in diethyl ether to the mixture;

adding the Compound (IIa) to the mixture;

heating the mixture to a temperature of about 50° C. to about 100° C., adding 1,2-dibromoethane and trimethylsilyl chloride, and agitating the mixture about 50° C. to about 100° C. for a time of about 8 hours to about 24 hours;

adding tetrakis(triphenylphosphine)palladium(0) and Compound (IIIa)

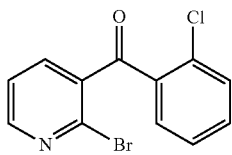
(IIIa)

to the mixture; and heating the mixture to a temperature of about 50° C. to about 100° C. to form Compound (I).

17. The process of claim 8, wherein the Compound (IV) is prepared according to a process comprising:

heating a mixture of Compound (V)

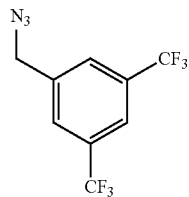
(V)

and Compound (VI)

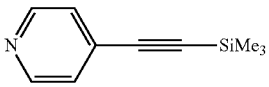
(VI)

to a temperature of about 95-105° C.;

adding heptane to the mixture; and crystallizing Compound (IV) from the heptane.

18. The process of claim 17, wherein the Compound (VI) is prepared according to a process comprising:

combining zinc bromide and a solvent, wherein the solvent is selected from the group consisting of: N,N-dimethylformamide, N,N-dimethylacetamide, tetrahydrofuran, diisopropyl ether, toluene, anisole, t-butylmethyl ether, diethyl ether, 1,4-dioxane, 1,2-dimethoxyethane, N-methylpyrrolidone, and dimethylsulfoxide;

adding 4-bromopyridine hydrochloride, triphenylphosphine, and palladium (II) chloride while maintaining the batch temperature between about 0° C. about 25° C.;

further adding triethylamine and trimethylsilylacetylene while maintaining the batch temperature between about 0° C. about 25° C.;

combining the reaction mixture with hexanes, and treating the reaction mixture with $NH_4OH$;

washing an organic phase of the reaction mixture first with $NH_4OH$ and then with water;

neutralizing the organic phase with hydrochloric acid;

drying the organic phase, and concentrating to a slurry, wherein drying the organic phase further comprises stirring with sodium sulfate or magnesium sulfate;

combining the slurry with hexanes to give a precipitate;

filtering the precipitate out of the slurry and concentrating a filtrate; and distilling the filtrate to produce Compound (VI).

19. The method of claim 16, wherein the Compound (IIIa)

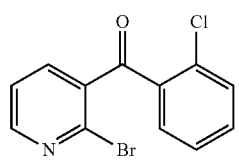
(IIIa)

is prepared by a process comprising:

contacting 2-bromopyridine with lithium diisopropylamine (LDA) in THF at about −70° C. to produce lithiated 2-bromopyridine;

contacting the lithiated 2-bromopyridine with Compound (VII)

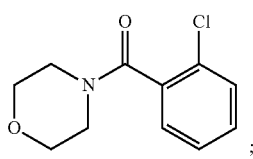

(VII)

washing the reaction mixture with aqueous HCl;
extracting the Compound (IIIa) from the reaction mixture into an organic layer and drying the organic layer;
concentrating the organic layer;
dissolving the residue in an organic solvent; and then crystallizing Compound (IIIa) from the solution.

20. The method of claim 19, wherein the lithiated 2-bromopyridine and Compound (VII) are allowed to react at a temperature of 65° C. or less; and
wherein the reaction is quenched by addition of methanol;
the Compound (IIIa) is extracted by addition of aqueous HCl and t-butyl methyl ether;
the organic phase is dried and concentrated;
the residue is solubilized in IPA; and
the Compound (IIIa) is crystallized by addition of heptane; and
wherein the Compound (VII) is prepared according to a process comprising: combining morpholine, toluene, Compound (IX)

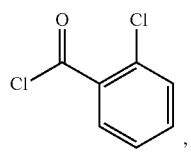

(IX)

and pyridine.

* * * * *